United States Patent
Shim et al.

(10) Patent No.: US 11,576,611 B2
(45) Date of Patent: Feb. 14, 2023

(54) WEARABLE DEVICE AND SENSOR DEVICE

(71) Applicant: SAMSUNG ELECTRONICS CO., LTD., Suwon-si (KR)

(72) Inventors: Jae Wook Shim, Yongin-si (KR); Hyun Seok Moon, Hwaseong-si (KR); Hyeong Seok Jang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 508 days.

(21) Appl. No.: 16/665,554

(22) Filed: Oct. 28, 2019

(65) Prior Publication Data
US 2020/0138373 A1     May 7, 2020

(30) Foreign Application Priority Data

Nov. 6, 2018 (KR) .................. 10-2018-0135412

(51) Int. Cl.
*A61B 5/00* (2006.01)
*G06F 3/02* (2006.01)
*G06F 1/16* (2006.01)

(52) U.S. Cl.
CPC .......... *A61B 5/6802* (2013.01); *A61B 5/0075* (2013.01); *G06F 1/163* (2013.01); *G06F 3/0202* (2013.01); *A61B 5/0006* (2013.01); *A61B 2560/04* (2013.01)

(58) Field of Classification Search
CPC ....... A61B 5/02; A61B 5/024; A61B 5/02416; A61B 5/1455; A61B 5/14551; A61B 5/14552; A61B 5/14532; A61B 5/14546; A61B 5/68; A61B 5/6802; A61B 5/6803; A61B 5/6804; A61B 5/6806; A61B 5/681; A61B 5/6807; A61B 5/6813; A61B 5/6824; A61B 5/6825; A61B 5/6826; A61B 5/683; A61B 5/6831; A61B 5/6833
See application file for complete search history.

(56) References Cited

U.S. PATENT DOCUMENTS

| | | |
|---|---|---|
| 8,805,464 B2 | 8/2014 | Onoe et al. |
| 2003/0181817 A1 | 9/2003 | Mori |
| 2009/0247885 A1 | 10/2009 | Suzuki et al. |
| 2010/0087717 A1 | 4/2010 | Onoe et al. |
| 2013/0017787 A1 | 1/2013 | Eshita |
| 2015/0208933 A1 | 7/2015 | Satomi et al. |
| 2015/0280129 A1 | 10/2015 | Kim et al. |
| 2018/0168505 A1 | 6/2018 | Kawai |
| 2019/0053759 A1 | 2/2019 | Cho et al. |

FOREIGN PATENT DOCUMENTS

| | | |
|---|---|---|
| JP | 2003-275183 A | 9/2003 |
| JP | 3496131 B2 | 2/2004 |
| JP | 3741147 B2 | 2/2006 |

(Continued)

*Primary Examiner* — Chu Chuan Liu
(74) *Attorney, Agent, or Firm* — Sughrue Mion, PLLC

(57) ABSTRACT

A wearable device includes a wearable device main body, a sensor part configured to contact a skin surface of a user of the wearable device, and measure a bio-signal of the user, and a shock absorber that is interposed between the wearable device main body and the sensor part to mechanically connect the wearable device main body and the sensor part, and that is configured to reduce motion transmission between the wearable device main body and the sensor part to permit the wearable device main body to move independently from the sensor part.

6 Claims, 6 Drawing Sheets

(56) References Cited

FOREIGN PATENT DOCUMENTS

| | | |
|---|---|---|
| JP | 2007-296266 A | 11/2007 |
| JP | 4186374 B2 | 11/2008 |
| JP | 2009-226167 A | 10/2009 |
| JP | 4493729 B2 | 6/2010 |
| JP | 2014-68733 A | 4/2014 |
| JP | 2016-096977 A | 5/2016 |
| JP | 2017-064055 A | 4/2017 |
| KR | 10-1668022 B1 | 10/2016 |
| KR | 10-2017-0056933 A | 5/2017 |
| KR | 10-2018-0082762 A | 7/2018 |

WEARABLE DEVICE AND SENSOR DEVICE

CROSS-REFERENCE TO RELATED APPLICATION(S)

This application is based on and claims priority under 35 U.S.C. § 119 to Korean Patent Application No. 10-2018-0135412, filed on Nov. 6, 2018, in the Korean Intellectual Property Office, the disclosure of which is incorporated by reference herein in its entirety.

BACKGROUND

1. Field

The disclosure relates to technology for measuring bio-signals.

2. Description of Related Art

Healthcare technology is receiving a lot of attention as our society is rapidly aging, and social problems, such as the increase in healthcare costs and the like, are caused by the aging society. Accordingly, medical devices for use in hospitals or medical examination institutions, and also small medical devices that individuals can carry are being developed.

Furthermore, such small medical devices are provided in the form of wearable devices worn by users to measure bio-signals, so that the users can directly measure and manage health conditions.

Therefore, much research has been conducted recently to manufacture devices for stably measuring bio-signals by applying a sensor for measuring bio-signals to wearable devices.

SUMMARY

Provided are a wearable device and a sensor device.

Additional aspects will be set forth in part in the description which follows and, in part, will be apparent from the description, or may be learned by practice of the presented embodiments.

In accordance with an aspect of the disclosure, a wearable device includes a wearable device main body, a sensor part configured to contact a skin surface of a user of the wearable device, and measure a bio-signal of the user, and a shock absorber that is interposed between the wearable device main body and the sensor part to mechanically connect the wearable device main body and the sensor part, and that is configured to reduce motion transmission between the wearable device main body and the sensor part to permit the wearable device main body to move independently from the sensor part.

The sensor part may include a sensor configured to measure the bio-signal of the user, a plate configured to support the sensor, and a skin adhering member configured to permit the sensor to adhere to the skin surface of the user.

The sensor part may include a buffer member that is provided between the plate and the sensor, and that is configured to permit a first shape of a skin contact surface of the sensor part to adapt to a second shape of a curved portion of the skin surface of the user.

The shock absorber may be formed with horizontal and vertical gaps.

The shock absorber may be formed with a plurality of horizontal corrugations disposed in a vertical direction.

The wearable device main body may include a sensor accommodating space formed at a bottom portion, and the sensor part and the shock absorber are disposed in the sensor accommodating space.

The shock absorber may include an elastic member that is provided between a top surface of the sensor accommodating space and a top surface of the sensor part, and that is configured to permit a vertical position of the sensor part to be maintained in the sensor accommodating space, and a buffer member that is provided between a left surface of the sensor accommodating space and a left surface of the sensor part, that is provided between a right surface of the sensor accommodating space and a right surface of the sensor part, and that is configured to mechanically connect the wearable device main body and the sensor part.

The buffer member may be formed with horizontal and vertical gaps.

The buffer member may be formed with a plurality of concentric corrugations disposed in a horizontal direction.

A surface of the elastic member that contacts the sensor part may be coated to reduce a friction coefficient.

In accordance with an aspect of the disclosure, a sensor device may include a sensor that is configured to contact a skin surface of a user, and measure a bio-signal of the user, a coil that is configured to receive power via electromagnetic induction from a wearable device, a stabilization circuit configured to store power received via the coil from the wearable device, and to stabilize a voltage, a near field communication (NFC) antenna configured to communicate with the wearable device via NFC, and a skin adhering member configured to permit the sensor to adhere to the skin surface of the user.

The NFC antenna may be configured to operate in a reader mode based on setting a parameter of the sensor device, and operate in a tag mode based on transmitting data generated by the sensor device.

The stabilization circuit may include a plurality of capacitors.

The coil and the NFC antenna may be formed in a concentric ring shape.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings and the detailed description, unless otherwise described, the same drawing reference numerals may refer to the same elements, features, and structures. The relative size and depiction of these elements may be exaggerated for clarity, illustration, and convenience.

DETAILED DESCRIPTION

Figure 1:
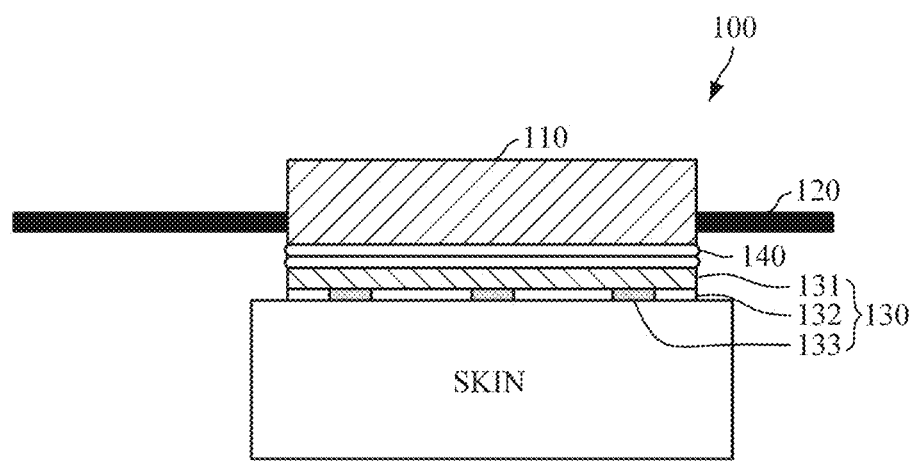
FIG. 1 is a diagram illustrating an example of a wearable device according to an embodiment.

Hereinafter, embodiments of the present disclosure will be described in detail with reference to the accompanying drawings. It should be noted that wherever possible, the same reference symbols may refer to the same elements, features, and structures illustrated in other drawings. In the following description, a detailed description of known functions and configurations incorporated herein may be omitted so as not to obscure the subject matter of the present disclosure.

It will be understood that, although the terms "first," "second," etc. may be used herein to describe various elements, these elements should not be limited by these terms. These terms may be used to distinguish one element from another. Any references to singular forms of terms may include the plural forms of the terms unless expressly stated otherwise. In the present specification, it should be understood that the terms, such as "including" or "having," etc., may indicate the existence of the features, numbers, steps, actions, components, parts, or combinations thereof, disclosed in the specification, and might not preclude the possibility that one or more other features, numbers, steps, actions, components, parts, or combinations thereof, may exist or may be added.

Further, components described in the specification may be discriminated according to functions mainly performed by the components. That is, two or more components may be integrated into a single component. Furthermore, a single component may be separated into two or more components. Moreover, each component may additionally perform some or all of a function executed by another component in addition to the main function thereof. Some or all of the main function of each component may be carried out by another component. Each component may be implemented in hardware or software, or a combination thereof.

The wearable device of the present disclosure is a device configured to be worn on a human body, and may be worn at various positions such as the wrist, thigh, arm, ankle, waist, head, neck, and the like. Examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like.

Further, the wearable device may be used alone or in connection with other electronic devices. In an embodiment, the wearable device may be connected to another electronic device via a communication interface, and may communicate with the other electronic device via the communication interface. In this case, the wearable device may provide information to the other electronic device to be output via the other electronic device, may receive information from the electronic device and output the information received from the electronic device, and/or may output the information simultaneously with the other electronic device. In an embodiment, the output information may be visually output via a display device, may be audibly output via a speaker device, or may be haptically output via vibrations, and the like. In an embodiment, the communication interface may be a short range communication interface such as a wireless fidelity (Wi-Fi) communication interface, a Bluetooth communication interface, an infrared communication interface, a Near Field Communication (NFC) interface, and the like.

Figure 2:
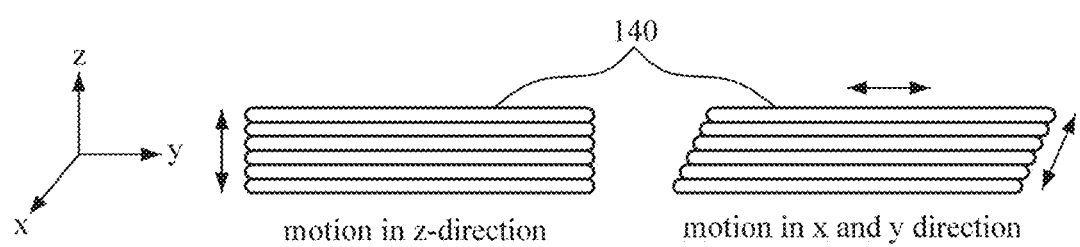
FIG. 2 is a diagram illustrating an example of a structure of a shock absorber according to an embodiment.

FIG. 1 is a diagram illustrating an example of a wearable device according to an embodiment, and FIG. 2 is a diagram illustrating an example of a structure of a shock absorber according to an embodiment. The wearable device of FIG. 1 may be a wristwatch-type wearable device configured to be worn on the wrist of a human body, but is not limited thereto.

Referring to FIGS. 1 and 2, the wearable device 100 includes a wearable device main body 110, a strap 120, a sensor part 130, and a shock absorber 140.

The wearable device main body 110 may include various electronic components for operation of the wearable device 100. For example, the wearable device main body 110 may include various electronic components such as a battery, a memory, a processor, a camera, a communication interface, a speaker, a microphone, a display, and the like.

The strap 120 may be connected to both ends of the wearable device main body 110, and may be fastened in a detachable manner or may be integrally formed as a smart band. The strap 120 may be made of a flexible material configured to be wrapped around a user's wrist so that the wearable device main body 110 may be worn on the wrist.

The sensor part 130 may measure a bio-signal of a user wearing the wearable device 100. The sensor part 130 includes a plate 131, a skin adhering member 132, and a sensor 133.

The plate 131 may support the sensor 133. The plate 131 may be made of a rigid material or a flexible material.

The sensor 133 may measure a bio-signal of a user. The sensor 133 may include various sensors such as an electromyogram (EMG) sensor, an electroencephalogram (EEG) sensor, a photoplethysmogram (PPG) sensor, an electrocardiogram (ECG) sensor, an infrared (IR) sensor, a bio-impedance sensor, a body temperature sensor, and the like. However, this is merely exemplary, and the sensor 133 is not limited thereto. That is, the sensor 133 may include various sensors which may measure bio-signals of a user.

The skin adhering member 132 may be provided at a skin contacting portion of the sensor part 130. In an embodiment, the skin adhering member 132 may be made of a flexible, stretchable, sticky, and bio-compatible material, to enable the sensor 133 to tightly contact (e.g., adhere to) the skin. For example, the skin adhering member 132 may be made of polydimethylsiloxane (PDMS), oligosiloxane, polyurethane (PU), polystyrene (PS), polycarbonate (PC), an acrylic adhesive material, and the like.

The shock absorber 140 may be interposed between the wearable device main body 110 and the sensor part 130, and may mechanically connect the wearable device main body 110 and the sensor part 130. The shock absorber 140 may reduce motion transmission between the wearable device main body 110 and the sensor part 130, and may permit the wearable device main body 110 and the sensor part 130 to move independently from each other.

In an embodiment, the shock absorber 140 may be made of a flexible and stretchable material (e.g., a polymer, a plastic, etc.) having horizontal and vertical gaps. For example, as illustrated in FIG. 2, the shock absorber 140 may be made of a flexible and stretchable material having a plurality of horizontal corrugations disposed in a vertical direction.

The shock absorber 140 may reduce horizontal motion of the wearable device main body 110 from being transmitted to the sensor part 130, and may reduce vertical motion of the wearable device main body 110 from causing a change in skin contact pressure of the sensor part 130.

In addition, the sensor part 130 may further include a buffer member, which is provided between the plate 131 and the sensor 133, to allow a skin contact surface of the sensor part 130 to change according to a curved portion of the skin. That is, the buffer member may permit a shape of the skin contact surface of the sensor part 130 to adapt to a shape of a skin surface of a user. In an embodiment, the buffer member may be made of sponge, latex, and the like, but this is merely exemplary, and is not limited thereto.

The wearable device main body 110 and the sensor 133 may be connected to each other via a wired connection or a wireless connection, and may communicate with each other via the connection. That is, sensor data of the sensor 133 may be transmitted to the wearable device main body 110 which is connected to the sensor 133, and the wearable device main body 110 may receive and process the sensor data of the sensor 133.

Figure 3:
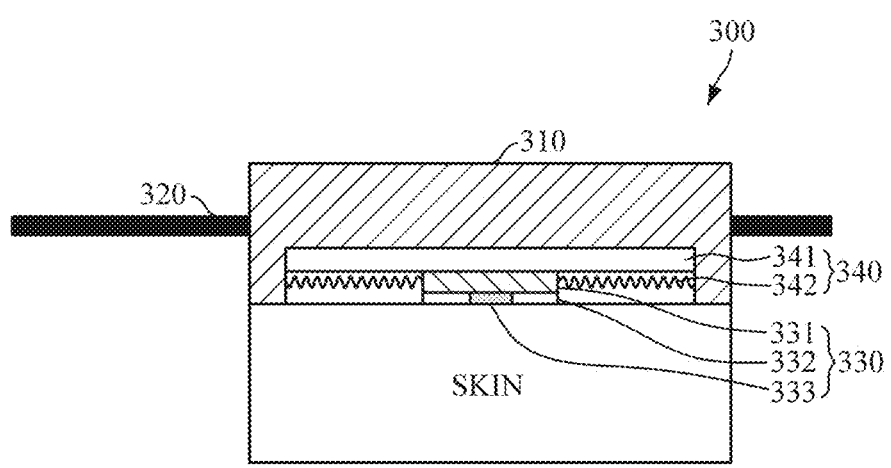
FIG. 3 is a diagram illustrating another example of a wearable device according to an embodiment.
Figure 4:
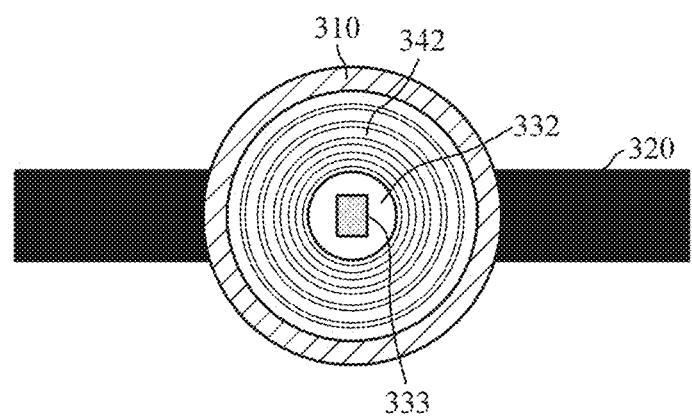
FIG. 4 is a diagram illustrating an example of a bottom view of a wearable device according to an embodiment.

FIG. 3 is a diagram illustrating another example of a wearable device according to an embodiment, and FIG. 4 is a diagram illustrating an example of a bottom view of a wearable device according to an embodiment. The wearable device of FIG. 3 may be a wristwatch-type wearable device configured to be worn on the wrist of a human body, but is not limited thereto.

Referring to FIGS. 3 and 4, the wearable device 100 includes a wearable device main body 310, a strap 320, a sensor part 330, and a shock absorber 340.

The wearable device main body 310 may include various electronic components for operation of the wearable device 300. For example, the wearable device main body 310 may include a battery, a memory, a processor, a camera, a communication interface, a speaker, a microphone, a display, and the like.

The wearable device main body 310 may have a sensor accommodating space formed at the bottom of the wearable device main body 310 to accommodate the sensor part 330.

The strap 320 may be connected to both ends of the wearable device main body 310, and may be fastened in a detachable manner or may be integrally formed as a smart band. The strap 320 may be made of a flexible material configured to be wrapped around a user's wrist so that the wearable device main body 310 may be worn on the wrist.

The sensor part 330 may be disposed in the sensor accommodating space of the wearable device main body 310, and may contact a skin surface of a user wearing the wearable device 300 to measure a bio-signal of the user. The sensor part 330 includes a plate 331, a skin adhering member 332, and a sensor 333.

The plate 331 may support the sensor 333. The plate 331 may be made of a rigid material or a flexible material.

The sensor 333 may measure a bio-signal of a user. The sensor 333 may include various sensors such as an EMG sensor, an EEG sensor, a PPG sensor, an ECG sensor, an IR sensor, a bio-impedance sensor, a body temperature sensor, and the like. However, this is merely exemplary, and the sensor 333 is not limited thereto. That is, the sensor 333 may include various sensors that may measure bio-signals of the user.

The skin adhering member 332 may be provided at a skin contacting portion of the sensor part 330. In an embodiment, the skin adhering member 332 may be made of a flexible, stretchable, sticky, and bio-compatible material, to enable the sensor 333 to tightly contact (e.g., adhere to) the skin. For example, the skin adhering member 332 may be made of PDMS, oligosiloxane, PU, PS, PC, an acrylic adhesive material, and the like.

The shock absorber 340 may be interposed between the wearable device main body 310 and the sensor part 330, may be disposed in the sensor accommodating space of the wearable device main body 310, and may mechanically connect the wearable device main body 310 and the sensor part 330. The shock absorber 340 may reduce motion transmission between the wearable device main body 310 and the sensor part 330, and may permit the wearable device main body 310 and the sensor part 330 to move independently from each other. The shock absorber 340 may include an elastic member 341 and a buffer member 342.

The elastic member 341 may be provided between a top surface of the sensor accommodating space of the wearable device main body 310 and a top surface of the sensor part 330, and may permit the vertical position of the sensor part 330 to be maintained. In an embodiment, the elastic member 341 may be made of sponge, latex, and the like, but this is merely exemplary, and is not limited thereto. A surface of the elastic member 341 that contacts the sensor part 330 may be coated so that a friction coefficient may be reduced or minimized. In this way, the elastic member 341 may reduce or minimize transmission of a horizontal motion of the wearable device main body 110 to the sensor part 330.

The buffer member 342 may be provided between left and right surfaces of the sensor accommodating space of the wearable device main body 310 and left and right surfaces of the sensor part 330, and may mechanically connect the wearable device main body 310 and the sensor part 330. The buffer member 342 may reduce motion transmission between the wearable device main body 310 and the sensor part 330, and may permit the wearable device main body 310 and the sensor part 330 to move independently from each other.

In an embodiment, the buffer member 342 may be made of a flexible and stretchable material (e.g., a polymer, a plastic, etc.) having horizontal and vertical gaps. For example, as illustrated in FIG. 4, the buffer member 342 may be formed with a plurality of concentric corrugations disposed in a horizontal direction.

In addition, the sensor part 330 may further include a buffer member, which is provided between the plate 331 and the sensor 333, and that may allow a skin contact surface of the sensor part 330 to change according to a curved portion of the skin. That is, the buffer member may permit a shape of the skin contact surface of the sensor part 330 to adapt to a shape of a skin surface of a user. In an embodiment, the buffer member may be made of sponge, latex, and the like, but this is merely exemplary, and is not limited thereto.

The wearable device main body 310 and the sensor 333 may be connected to each other via a wired connection or a wireless connection, and may communicate with each other via the connection. That is, sensor data of the sensor 333 may be transmitted to the wearable device main body 310 which is connected to the sensor 333, and the wearable device main body 310 may receive and process the sensor data of the sensor 333.

Figure 5:
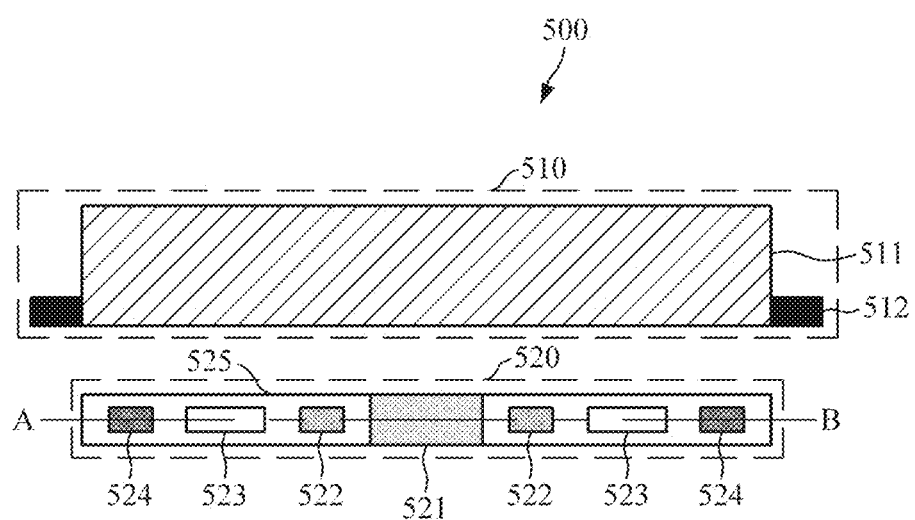
FIG. 5 is a diagram illustrating an example of a sensor system according to an embodiment.
Figure 6:
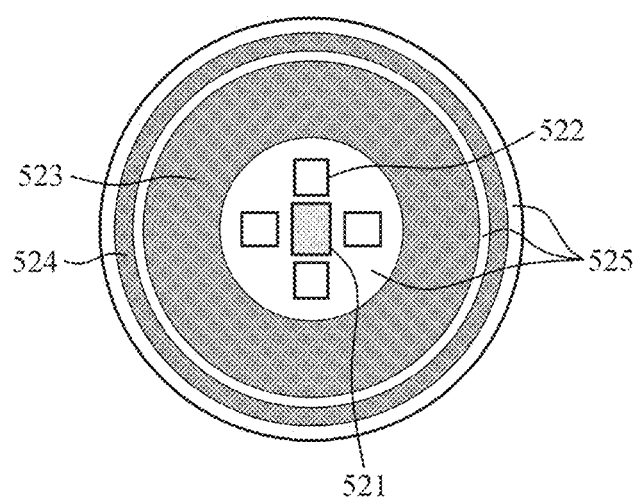
FIG. 6 is a diagram illustrating an example of a cross-sectional view as taken along line A-B of FIG. 5 according to an embodiment.

FIG. 5 is a diagram illustrating an example of a sensor system according to an embodiment, and FIG. 6 is a diagram illustrating an example of a cross-sectional view as taken along line A-B of FIG. 5 according to an embodiment.

Referring to FIG. 5, the sensor system 500 includes a wearable device 510 and a sensor device 520.

The wearable device 510 includes a main body 511 and a strap 512.

The main body 511 may include various electronic components for operation of the wearable device 510. For example, the main body 511 may include a battery, a memory, a processor, a camera, a communication interface, a speaker, a microphone, a display, and the like.

The main body 511 may be completely independent from the sensor device 520 mechanically, and may communicate bidirectionally with the sensor device 520 using NFC or another type of short range protocol. In an embodiment, when setting a parameter of the sensor device 520, the main body 511 operates in a tag mode, and the sensor device 520 operates in a reader mode; and when reading data measured by the sensor device 520, the sensor device 520 operates in a tag mode, and the main body 511 operates in a reader mode.

The main body 511 may wirelessly supply power to the sensor device 520. For example, the main body 511 may wirelessly supply power to the sensor device 520 using electromagnetic induction. To this end, the main body 511 may include a coil.

The strap 512 may be connected to both ends of the main body 511, and may be fastened in a detachable manner or may be integrally formed as a smart band. The strap 512 may be made of a flexible material configured to be wrapped around a user's wrist so that the main body 511 may be worn on the wrist.

The sensor device 520 may measure a bio-signal of a user. The sensor device 520 includes a sensor 521, a stabilization circuit 522, a coil 523, an NFC antenna 524, and a skin adhering member 525.

The sensor 521 may measure a bio-signal of a user. The sensor 521 may include various sensors such as an EMG sensor, an EEG sensor, a PPG sensor, an ECG sensor, an IR sensor, a bio-impedance sensor, a body temperature sensor, and the like. However, this is merely exemplary, and the sensor 521 is not limited thereto. That is, the sensor 521 may include various sensors which may measure bio-signals of a user.

The stabilization circuit 522 may store power wirelessly supplied from the wearable device 510, and may stabilize voltage by filtering. To this end, the stabilization circuit 522 may include various capacitors.

The coil 523 may be used to receive power wirelessly by electromagnetic induction from the wearable device 510. As the sensor device 520 receives power by electromagnetic induction from the wearable device 510, the sensor device 520 may operate without a separate battery.

The NFC antenna 524 may perform bidirectional NFC with the wearable device 510. In an embodiment, when setting a parameter of the sensor device 520, the wearable device 510 operates in a tag mode, and the NFC antenna 524 operates in a reader mode, and when transmitting data generated by the sensor device 520, the NFC antenna 524 operates in a tag mode, and the wearable device 510 operates in a reader mode.

The skin adhering member 525 may be provided at a skin contacting portion of the sensor device 520. In an embodiment, the skin adhering member 525 may be made of a flexible, stretchable, sticky, and bio-compatible material, to enable the sensor 521 to tightly contact (e.g., adhere to) the skin. For example, the skin adhering member 525 may be made of PDMS, oligosiloxane, PU, PS, PC, an acrylic adhesive material, and the like.

In an embodiment, and as illustrated in FIG. 6, the sensor device 520 may be formed in a circular shape, with the sensor 521 being formed at the center of the sensor device 520, and four stabilization circuits 522 being formed to surround the sensor 521. Further, the coil 523 may be formed in a ring shape to surround the four stabilization circuits 522, and the NFC antenna 524 may be formed in a ring shape to surround the coil 523. In this case, the coil 523 and the NFC antenna 524 may be formed in a concentric ring shape.

The arrangements and shapes of the components of the sensor device 520 of FIG. 6 are merely exemplary, and are not limited thereto. That is, there may be various arrangements and shapes of the components of the sensor device 520, and may vary depending on the size and shape of the sensor device 520.

In addition, the wearable device 510 may be worn above the sensor device 520. Accordingly, a contact surface between the wearable device 510 and the sensor device 520 may be coated to reduce or minimize a frictional force therebetween.

The present disclosure has been described herein with regard to various embodiments. However, it should be obvious to those skilled in the art that various changes and modifications can be made without departing from the scope of the present disclosure. Thus, it should be understood that the above-described embodiments are illustrative in all aspects and are not intended to limit the present disclosure.

What is claimed is:

1. A wearable device comprising:
a wearable device main body;
a sensor part configured to contact a skin surface of a user of the wearable device, and measure a bio-signal of the user; and
a shock absorber that is interposed between the wearable device main body and the sensor part to mechanically connect the wearable device main body and the sensor part, and that is configured to reduce motion transmission between the wearable device main body and the sensor part to permit the wearable device main body to move independently from the sensor part;
wherein the shock absorber is formed with a plurality of elongated corrugations.

2. The wearable device of claim 1, wherein the sensor part comprises:
a sensor configured to measure the bio-signal of the user;
a plate configured to support the sensor; and
a skin adhering member configured to permit the sensor to adhere to the skin surface of the user.

3. The wearable device of claim 2, wherein the sensor part further comprises:
a buffer member that is provided between the plate and the sensor, and that is configured to permit a first shape of a skin contact surface of the sensor part to adapt to a second shape of a curved portion of the skin surface of the user.

4. The wearable device of claim 1, wherein the shock absorber is formed with horizontal and vertical gaps.

5. The wearable device of claim 4, wherein the plurality of elongated corrugations include a plurality of horizontal corrugations disposed in a vertical direction.

6. The wearable device of claim 1, wherein the plurality of elongated corrugations include a plurality of horizontal corrugations disposed in a vertical direction.

* * * * *